(12) United States Patent
Huang et al.

(10) Patent No.: US 11,950,902 B2
(45) Date of Patent: Apr. 9, 2024

(54) MICRO BIOSENSOR AND METHOD FOR REDUCING MEASUREMENT INTERFERENCE USING THE SAME

(71) Applicant: Bionime Corporation, Taichung (TW)

(72) Inventors: Chun-Mu Huang, Taichung (TW);
Chieh-Hsing Chen, Taichung (TW);
Heng-Chia Chang, Taichung (TW);
Chi-Hao Chen, Taichung (TW);
Pi-Hsuan Chen, Taichung (TW)

(73) Assignee: Bionime Corporation, Taichung (TW)

( * ) Notice: Subject to any disclaimer, the term of this patent is extended or adjusted under 35 U.S.C. 154(b) by 360 days.

(21) Appl. No.: 16/944,328

(22) Filed: Jul. 31, 2020

(65) Prior Publication Data
US 2021/0030324 A1    Feb. 4, 2021

Related U.S. Application Data

(60) Provisional application No. 62/988,549, filed on Mar. 12, 2020, provisional application No. 62/882,162, filed on Aug. 2, 2019.

(51) Int. Cl.
*A61B 5/145* (2006.01)
*A61B 5/1473* (2006.01)
*A61B 5/1486* (2006.01)

(52) U.S. Cl.
CPC ........ *A61B 5/14503* (2013.01); *A61B 5/1451* (2013.01); *A61B 5/14532* (2013.01);
(Continued)

(58) Field of Classification Search
CPC ............ A61B 5/14532; A61B 5/14735; A61B 5/14865; A61B 2560/0468; A61B 5/1486; A61B 5/1468; A61B 5/1495
See application file for complete search history.

(56) References Cited

U.S. PATENT DOCUMENTS

RE43,399 E    5/2012  Simpson et al.
8,326,393 B2  12/2012 Kotzan et al.
(Continued)

FOREIGN PATENT DOCUMENTS

CN   104535627 A   4/2015
CN   109283234 A   1/2019
(Continued)

OTHER PUBLICATIONS

European Search Report dated Nov. 17, 2020 cited in application EP 20 18 8965.
(Continued)

*Primary Examiner* — David J. McCrosky
*Assistant Examiner* — Clarissa Cuevas
(74) *Attorney, Agent, or Firm* — Perkins Coie LLP; Sean Lee; Viola Kung

(57) ABSTRACT

The present invention provides a micro biosensor for reducing a measurement interference when measuring a target analyte in the biofluid, including: a substrate; a first working electrode configured on the surface, and including a first sensing section; a second working electrode configured on the surface, and including a second sensing section which is configured adjacent to at least one side of the first sensing section; and a chemical reagent covered on at least a portion of the first sensing section for reacting with the target analyte to produce a resultant. When the first working electrode is driven by a first working voltage, the first sensing section measures a physiological signal with respect to the target analyte. When the second working electrode is driven by a second working voltage, the second conductive material can directly consume the interferant so as to continuously reduce the measurement inference of the physiological signal.

15 Claims, 22 Drawing Sheets

(52) U.S. Cl.
CPC ........ *A61B 5/14546* (2013.01); *A61B 5/1473* (2013.01); *A61B 5/14735* (2013.01); *A61B 5/14865* (2013.01); *A61B 2560/0223* (2013.01); *A61B 2560/0468* (2013.01); *A61B 2562/0215* (2017.08); *A61B 2562/028* (2013.01); *A61B 2562/125* (2013.01); *A61B 2562/16* (2013.01)

(56) References Cited

U.S. PATENT DOCUMENTS

| | | | |
|---|---|---|---|
| 8,620,398 | B2 | 12/2013 | Feldman et al. |
| 9,326,714 | B2 | 5/2016 | Say et al. |
| 9,504,413 | B2 | 11/2016 | Simpson et al. |
| 10,321,865 | B2 | 6/2019 | Gautham et al. |
| 10,327,678 | B2 | 6/2019 | Gottlieb et al. |
| 2005/0139469 | A1 | 6/2005 | Davies et al. |
| 2010/0094110 | A1 | 4/2010 | Heller et al. |
| 2010/0270180 | A1 | 10/2010 | Liu et al. |
| 2010/0324400 | A1* | 12/2010 | Say ............... A61M 5/1723 600/365 |
| 2011/0155586 | A1* | 6/2011 | Elibol ............ G01N 27/3278 204/403.01 |
| 2011/0259741 | A1 | 10/2011 | Murase et al. |
| 2013/0131478 | A1* | 5/2013 | Simpson .......... A61B 5/7203 600/347 |
| 2013/0245412 | A1 | 9/2013 | Rong et al. |
| 2014/0005508 | A1* | 1/2014 | Estes ............... A61B 5/1495 600/347 |
| 2019/0076070 | A1* | 3/2019 | Nogueira ......... A61B 5/1468 |
| 2019/0216374 | A1* | 7/2019 | Hoss ............... A61B 5/1473 |
| 2019/0239778 | A1 | 8/2019 | Srinivasan et al. |
| 2020/0266393 | A1* | 8/2020 | Tang ............... H01L 51/56 |

FOREIGN PATENT DOCUMENTS

| | | | |
|---|---|---|---|
| CN | 109298032 | A | 2/2019 |
| EP | 3220137 | B1 | 1/2019 |
| IN | 105891297 | A | 8/2016 |
| IN | 106290530 | A | 1/2017 |
| KR | 20160049340 | * | 2/2017 |
| TW | I427289 | B | 2/2014 |
| WO | 2005045413 | A1 | 5/2005 |

OTHER PUBLICATIONS

International Search Report dated Nov. 3, 2020 cited in PCT/CN2020/106386.

Bo Liang, et al., "An origami paper device for complete elimination of interferents in enzymatic electrochemical biosensors", Electrochemistry Communications 82 (2017) 43-46, Jul. 4, 2017.

* cited by examiner

MICRO BIOSENSOR AND METHOD FOR REDUCING MEASUREMENT INTERFERENCE USING THE SAME

CROSS-REFERENCE TO RELATED APPLICATION AND CLAIM OF PRIORITY

This application claims the benefit of U.S. Provisional Applications No. 62/882,162, filed on Aug. 2, 2019 and No. 62/988,549, filed on Mar. 12, 2020, in the United States Patent and Trademark Office, the disclosures of which are incorporated herein in their entirety by reference.

FIELD OF THE INVENTION

The present invention is related to a micro biosensor. Particularly, the present invention is related to a micro biosensor and method for reducing measurement interference when measuring a target analyte in a biofluid.

BACKGROUND OF THE INVENTION

According to the rapid growth of the population of chronic patients, the detection of analytes in a biofluid in a living body is very important for the diagnosis and monitoring of patients. In particular, effective monitoring of glucose concentration in the body is the key to the treatment of diabetes. Therefore, a continuous glucose monitoring (CGM) system is paid much attention in recent years. The system has many advantages over traditional biosensors such as painless from sampling finger blood and continuously monitoring a physiological parameter of one or more target analytes in a body fluid.

The continuous glucose monitoring system includes a biosensor based on enzyme, which is used to measure a physiological signal corresponding to the glucose concentration in the body. Specifically, the glucose oxidase (GOx) catalyzes the glucose reaction to produce gluconolactone and a reduced enzyme. The reduced enzyme transfers electrons of oxygen in the biofluid in the body to produce a by-product hydrogen peroxide ($H_2O_2$), and the glucose concentration is quantified by catalyzing an oxidation reaction of the by-product $H_2O_2$. However, if there are interferants, such as a main component of vitamin C—ascorbic acid (AA), a common component of analgesic—acetaminophen (AM), uric acid (UA), protein and glucose analogs in blood or tissue fluid, and the oxidation potential of the interferants is close to that of $H_2O_2$, electrochemical signals unrelated to the target analytes will be produced. Such interfering signals have to be reduced so that the measurement of the physiological parameter is reliable.

It is therefore the Applicant's attempt to deal with the above situations encountered in the prior art.

SUMMARY OF THE INVENTION

The micro biosensor of the present invention can be implanted under a skin of a living body to measure physiological parameters of analytes in a biofluid. The micro biosensor of the present invention includes two working electrodes composed of different conductive materials, wherein one of the working electrodes can consume the interferant that affects the measurement in the biofluid, so that the other working electrode can obtain more accurate measurement results when measuring.

In accordance with another aspect of the present disclosure, a micro biosensor for implantation under a skin to perform a measurement of a concentration of glucose in a biofluid is disclosed, wherein the micro biosensor reduces an interference of at least one interferant in the biofluid on the measurement. The micro biosensor includes: a substrate having a first surface and a second surface which are oppositely configured; a first working electrode including a first sensing section configured on the first surface of the substrate, wherein the first sensing section includes a first conductive material; a chemical reagent covered on at least a portion of the first conductive material of the first sensing section for reacting with the glucose in the biofluid to produce hydrogen peroxide; and at least one second working electrode configured on the first surface of the substrate, and including a second sensing section, wherein the second sensing section is configured adjacent to at least one side of the first sensing section, and the second sensing section includes a second conductive material different from the first conductive material, wherein: when the first working electrode is driven by a first working voltage to cause the first sensing section to have a first sensitivity to the hydrogen peroxide and produce a measurement range, the first conductive material reacts with the hydrogen peroxide to produce a current signal, and through a value of the current signal corresponding to the concentration, a physiological signal is obtained; when the first working electrode is driven by the first working voltage to cause the first conductive material to react with the interferant to produce an interfering current signal, the interfering current signal and the current signal are output together to interfere the physiological signal; and when the second working electrode is driven by a second working voltage, the second sensing section has a second sensitivity smaller than the first sensitivity to the hydrogen peroxide, and the second sensing section produce an interference eliminating range, which contacts a surrounding of the first working electrode and at least partially overlaps with the measurement range to consume the interferant for reducing a generation of the interfering current signal.

In accordance with one more aspect of the present disclosure, a micro biosensor for implantation under a skin to perform a measurement of a physiological parameter of a target analyte in a biofluid is disclosed, wherein the micro biosensor reduces an interference of at least one interferant in the biofluid on the measurement. The micro biosensor includes: a substrate having a surface; a first working electrode including a first sensing section configured on the surface, wherein the first sensing section includes a first conductive material; at least one second working electrode configured on the surface and including a second sensing section configured adjacent to at least one side of the first sensing section, wherein the second sensing section includes a second conductive material; and a chemical reagent covered on at least a portion of the first conductive material for reacting with the target analyte in the biofluid to produce a resultant, wherein: the first working electrode is driven by a first working voltage to cause the first conductive material to react with the resultant for outputting a physiological signal corresponding to the physiological parameter of the target analyte; and the second working electrode is driven by a second working voltage to allow the second conductive material to consume the interferant for reducing the interference on the physiological signal caused by the interferant.

In accordance with one more aspect of the present disclosure, a method for reducing a measurement interference of a target analyte is provided. The method includes steps of: providing a micro biosensor used to measure a physiological parameter of a target analyte in a biofluid, wherein the micro biosensor includes: a substrate having a surface; a first working electrode including a first sensing section configured on the surface, wherein the first sensing section includes a first conductive material; at least one second working electrode configured on the surface and including a second sensing section, wherein the second sensing section includes a second conductive material; and a chemical reagent covered on at least a portion of the first conductive material for reacting with the target analyte in the biofluid to produce a resultant; performing an interference eliminating action, wherein the interference eliminating action is to drive the second working electrode by a second working voltage to cause the second conductive material to consume an interferant in the biofluid for reducing the interference on the measurement caused by the interferant; and performing a measurement action, wherein the measurement action is to drive the first working electrode by a first working voltage to cause the first conductive material to react with the resultant to output a physiological signal corresponding to the physiological parameter of the target analyte.

BRIEF DESCRIPTION OF THE DRAWINGS

Other objectives, advantages and efficacies of the present invention will be described in detail below taken from the preferred embodiments with reference to the accompanying drawings.

FIGS. 13(A)-13(C) show schematic diagrams of the time relationship between the interference eliminating action and the measurement action during measurement using the micro biosensor of the present invention, wherein FIG. 13(A) shows that the interference eliminating action and the measurement action partially overlap, FIG. 13(B) shows that the interference eliminating action and the measurement action do not overlap, and FIG. 13(C) shows that the interference eliminating action and the measurement action completely overlap.

FIGS. 18(A)-18(B) show results of the interference eliminating test in vivo, wherein FIG. 18(A) is the measurement curve without the interference eliminating mechanism, and FIG. 18(B) is the measurement curve with the interference eliminating mechanism.

DETAILED DESCRIPTION OF THE PREFERRED EMBODIMENTS

Figure 1A:
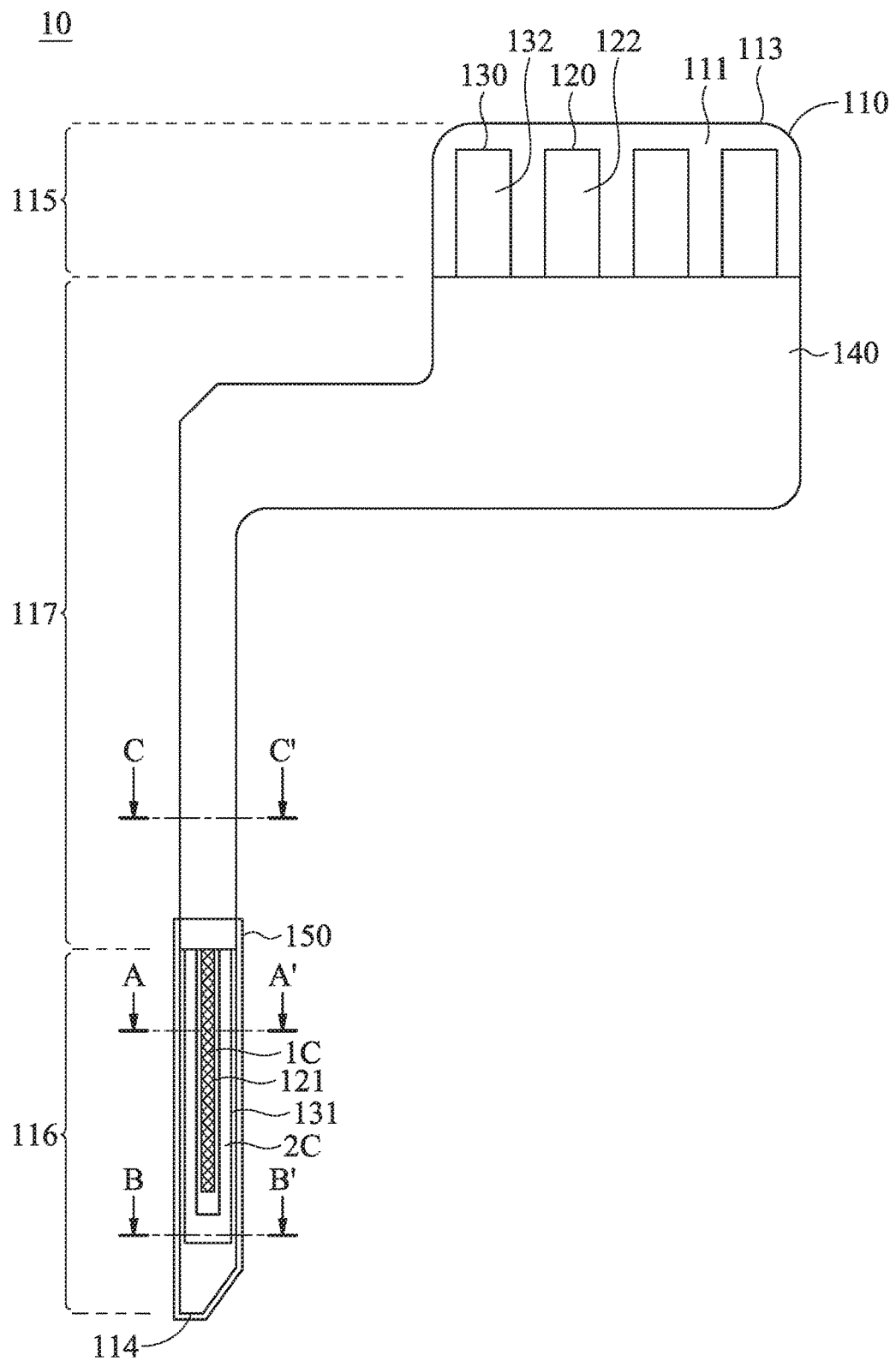
FIG. 1(A) shows a front schematic diagram of the first embodiment of the micro biosensor of the present invention.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed. In the preferred embodiments, the same reference numeral represents the same element in each embodiment.

The micro biosensor of the present invention can be a sensor of a continuous glucose monitoring system, which is used to be implanted under a skin of a living body to continuously measure physiological parameters of a target analyte in a biofluid. In addition, the term "target analyte" mentioned herein generally refers to any substance to be tested that exists in the living body, such as but not limited to glucose, lactose, uric acid, etc. The term "biofluid" may be but not limited to blood or interstitial fluid (ISF), and the term "physiological parameter" may be but not limited to concentration.

Figure 1B:
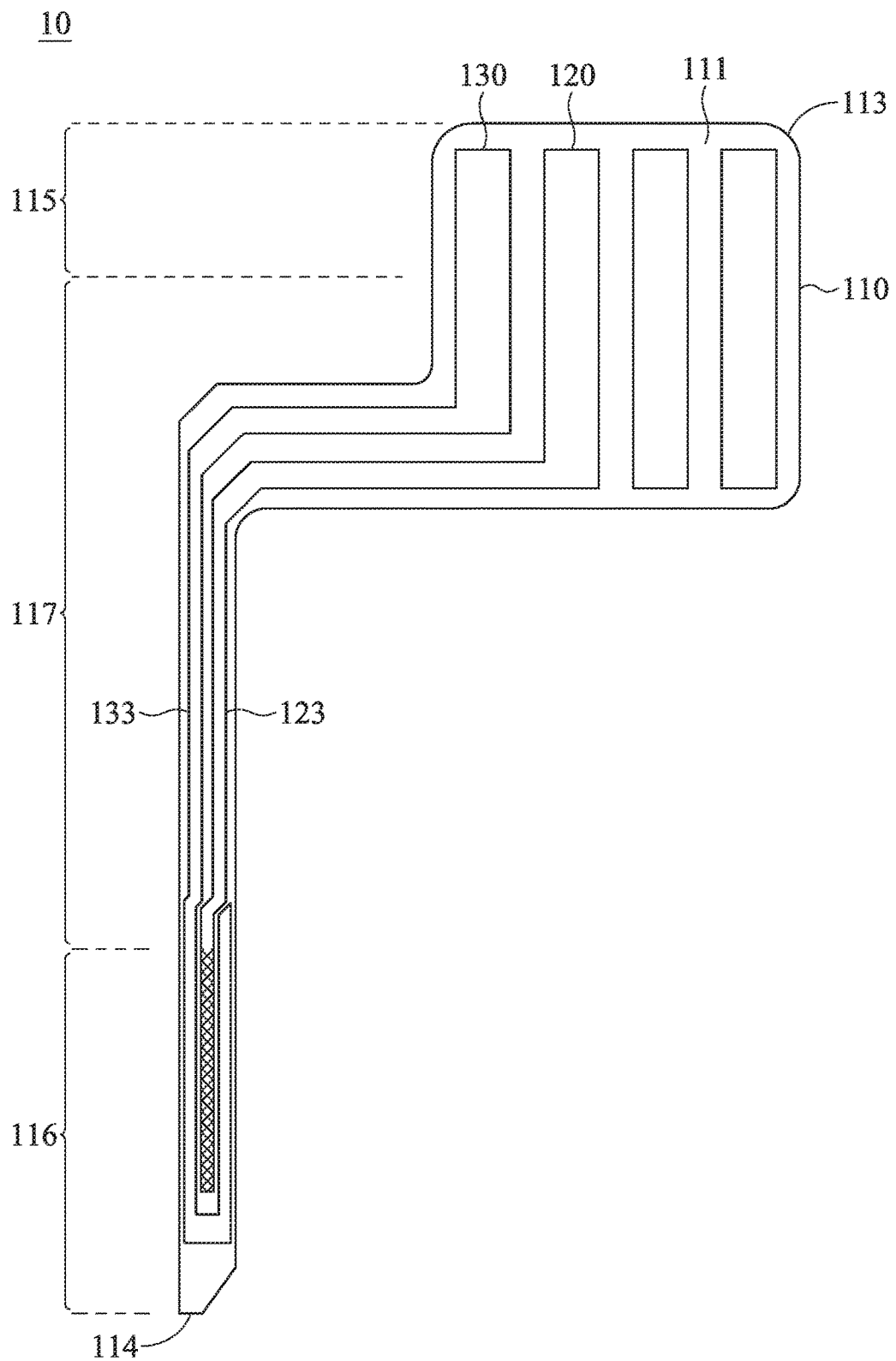
FIG. 1(B) shows a schematic diagram of the configuration of the first working electrode and the second working electrode of the first embodiment of the micro biosensor of the present invention.
Figure 2A:
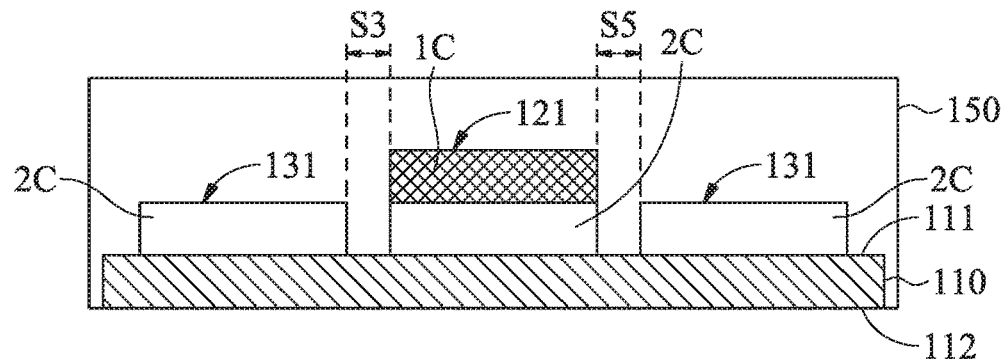
FIG. 2(A) shows a sectional schematic diagram of a cut view of the micro biosensor along the section line A-A' in FIG. 1(A).
Figure 9A:
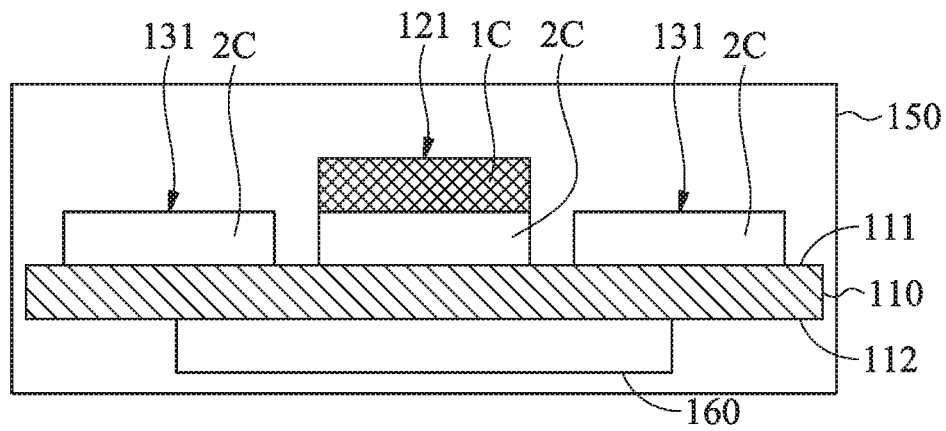
FIG. 9(A) shows a sectional schematic diagram of the sensing area of the micro biosensor of the present invention.
Figure 9B:
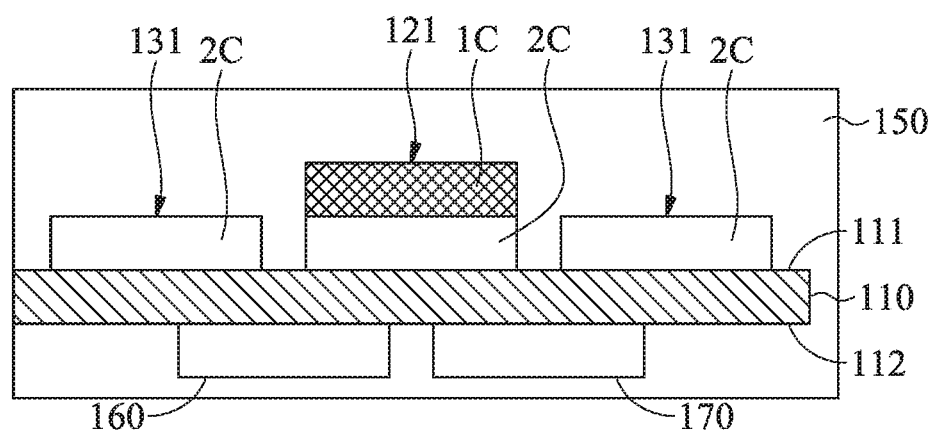
FIG. 9(B) shows a sectional schematic diagram of the sensing area of the micro biosensor of the present invention.

Please refer to FIG. 1(A), which is a front schematic diagram of a first embodiment of the micro biosensor of the present invention. The micro biosensor 10 of the present invention includes a substrate 110 having a surface 111, a first working electrode 120 and a second working electrode 130 configured on the surface 111, and an insulating layer 140 covering on a part of the surface 111, a part of the first working electrode 120 and a part of the second working electrode 130. Please refer to FIG. 1(B), the insulating layer 14 is removed in FIG. 1(B) to clearly show the configuration of the first working electrode 120 and the second working electrode 130 on the surface 111 of the substrate 110. The substrate 110 includes the surface 111, an opposite surface 112 (as shown in FIGS. 2(A), 9(A) and 9(B)), a first end 113, a second end 114, and further defines a signal output area 115, a sensing area 116, and an insulating area 117 thereon. The signal output area 115 is located at an area close to the first end 113, the sensing area 116 is located at an area close to the second end 114, and the insulating area 117 is coated by the insulating layer 140 and located at an area between the signal output area 115 and the sensing area 116. The first working electrode 120 and the second working electrode 130 are extended from the first end 113 to the second end 114 of the substrate 110. The first working electrode 120 includes a first sensing section 121 having a first conductive material 1C at the sensing area 116, a first signal output section 122 at the signal output area 115 (as shown in FIG. 1(A)), and a first signal connecting section 123 configured between the first sensing section 121 and the first signal output section 122 so as to be partially covered by at least a portion of the insulating area 117 (as shown in FIG. 1(B)). The second working electrode 130 includes a second sensing section 131 having a second conductive material 2C at the sensing area 116, a second signal output section 132 at the signal output area 115 (as shown in FIG. 1(A)), and a second signal connecting section 133 configured between the second sensing section 131 and the second signal output section 132 so as to be covered by at least a portion of the insulating area 117 (as shown in FIG. 1(B)). The second section 131 of the present invention is adjacent to at least one side of the first sensing section 121, and a side of the second sensing section 131 extends along the at least one side of the first sensing section 121. In the first embodiment, the second sensing section 131 extends along three sides of the first sensing section 121 to form a U-shape sensing section. Therefore, the first sensing section 121 and the second sensing section 131 of the present invention maintain a positional relationship therebetween only via the surface 111. Because the first sensing section 121 and the second sensing section 131 of the present invention are directly adjacent to each other, there are no intermediates, such as electrodes or connecting wires therebetween.

Figure 2B:
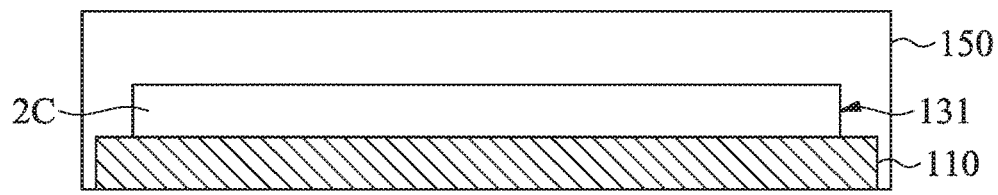
FIG. 2(B) shows a sectional schematic diagram of a cut view of the micro biosensor along the section line B-B' in FIG. 1(A).
Figure 2C:
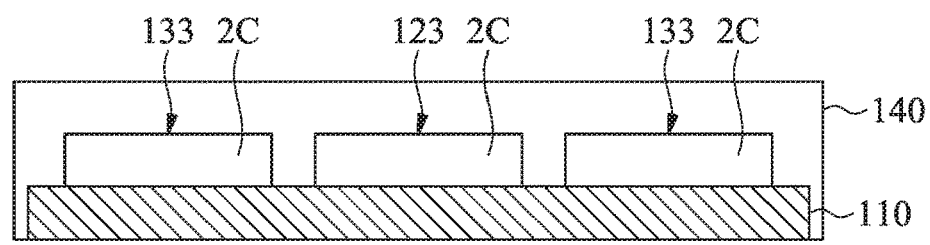
FIG. 2(C) shows a sectional schematic diagram of a cut view of the micro biosensor along the section line C-C' in FIG. 1(A).

In order to obtain these structures, in the manufacturing process, the second conductive material 2C can be formed on the surface 111 of the substrate 110 at first and patterned into a pattern as shown in FIG. 1(B). Specifically, the second conductive material 2C is divided into two separated areas, wherein one of the two areas extended from the first end 113 of the substrate 110 to the second end 114 and bent at the second end 114 to form the U-shape structure is preset as the second working electrode 130, and the other area extended from the first end 113 of the substrate 110 to the second end 114 and thus surrounded by the U-shaped structure is preset as the first working electrode 120. After the insulating layer 140 is covered on the substrate 110 and exposes the signal output area 115 and the sensing area 116, the first conductive material 1C is formed on the second conductive material 2C of the first working electrode 120 at the sensing area 116 to finish the manufacture of the first sensing section 121 of the first working electrode 120. However, although the figure does not show, the first conductive material 1C also can be only formed on the partially second conductive material 2C of the first working electrode 120 at the sensing area 116. Therefore, the sectional schematic diagrams of cut views of the micro biosensor along the section lines A-A', B-B' and C-C' in FIG. 1(A) of the present invention are shown in FIGS. 2(A), 2(B) and 2(C), respectively. In FIG. 2(A), the first sensing section 121 of the first embodiment of the present invention has the second conductive material 2C formed on the surface 111 of the substrate and topped with the first conductive material 1C, and the second sensing section 131 has the second conductive material 2C. FIG. 2(B) shows a bottom region of the U-shaped second sensing section 131, and thus, there is only the second conductive material 2C on the surface 111 of the substrate 110. In FIG. 2(C), because the first conductive material 1C is only formed at the sensing area 116, the portion of the first working electrode 120 located in the insulating region 117 has only the second conductive material 2C and is covered by the insulating layer 140.

Figure 2D:
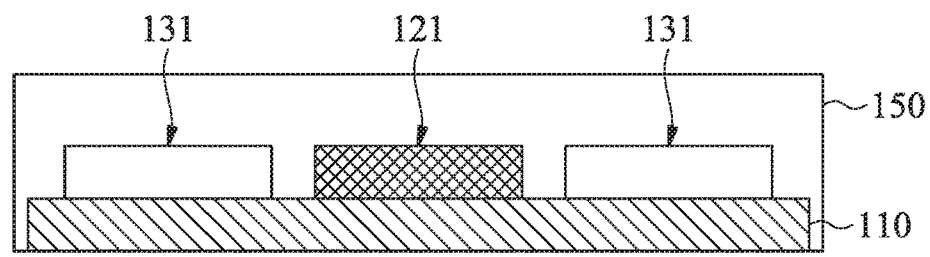
FIG. 2(D) shows a sectional schematic diagram of the sensing area of the micro biosensor obtained by another manufacturing process.

In another embodiment, the step of forming the insulating layer 140 also can be performed after forming the first conductive material 1C, and thus the first conductive material 1C also can be formed substantially on all the second conductive materials 2C of the first working electrode 120. In addition, the position, size and shape of the second conductive material 2C after the patterning step can be altered according to the demand in the present invention. Therefore, in other embodiment, the second conductive material 2C can be defined in the patterning step to present the pattern as shown in FIG. 1(B) but omitted at the area where the first sensing section 121 is expected to be formed. Specifically, the second conductive material 2C of the first working electrode 120 is only formed in the signal output area 115 and the insulating area 117, or at most extended to the partially sensing area 116. The first conductive material 1C is then formed on the surface 111 directly at the area where the first sensing section 121 is expected to be formed. The first conductive material 1C is electrically connected to the other portion (i.e. the second conductive material 2C) of the first working electrode 120 to finish the configuration of the first sensing section 121, and the sectional schematic diagram of the sensing area 116 of the micro biosensor 10 of this embodiment is shown as FIG. 2(D). In other embodiment, the second conductive material 2C within the area, where is expected to be formed the first working electrode 120, can be removed in the patterning step so that the first conductive material 1C can be directly formed thereon to form the first working electrode 120 before coating the insulating layer 140.

In the micro biosensor 10 of the present invention, a gap between the second sensing section 131 and the first sensing section 121 in the sensing area 116 is no larger than 0.2 mm. Preferably, the gap ranges from 0.01 mm to 0.2 mm. More preferably, the gap ranges from 0.01 mm to 0.1 mm. Further preferably, the gap ranges from 0.02 mm to 0.05 mm. Specifically, please refer to FIG. 2(A), in the first embodiment, the gaps S3 and S5 between the first sensing section 121 and the second sensing section 131 are both 0.04 mm.

In the present invention, the first conductive material 1C can be one of carbon, platinum, aluminum, gallium, gold, indium, iridium, iron, lead, magnesium, nickel, molybdenum, osmium, palladium, rhodium, silver, tin, titanium, zinc, silicon, zirconium, a derivative thereof (such as alloy, oxide or metal compound), or a combination thereof, and the second conductive material 2C can be the element or the derivative thereof exemplified for the first conductive material 1C. The material of the insulating layer 140 of the present invention can be any material that can achieve an insulating effect, such as, but not limited to, parylene, polyimide, polydimethylsiloxane (PDMS), liquid crystal Polymer material (LCP) or SU-8 photoresist of MicroChem, etc.

Figure 3A:
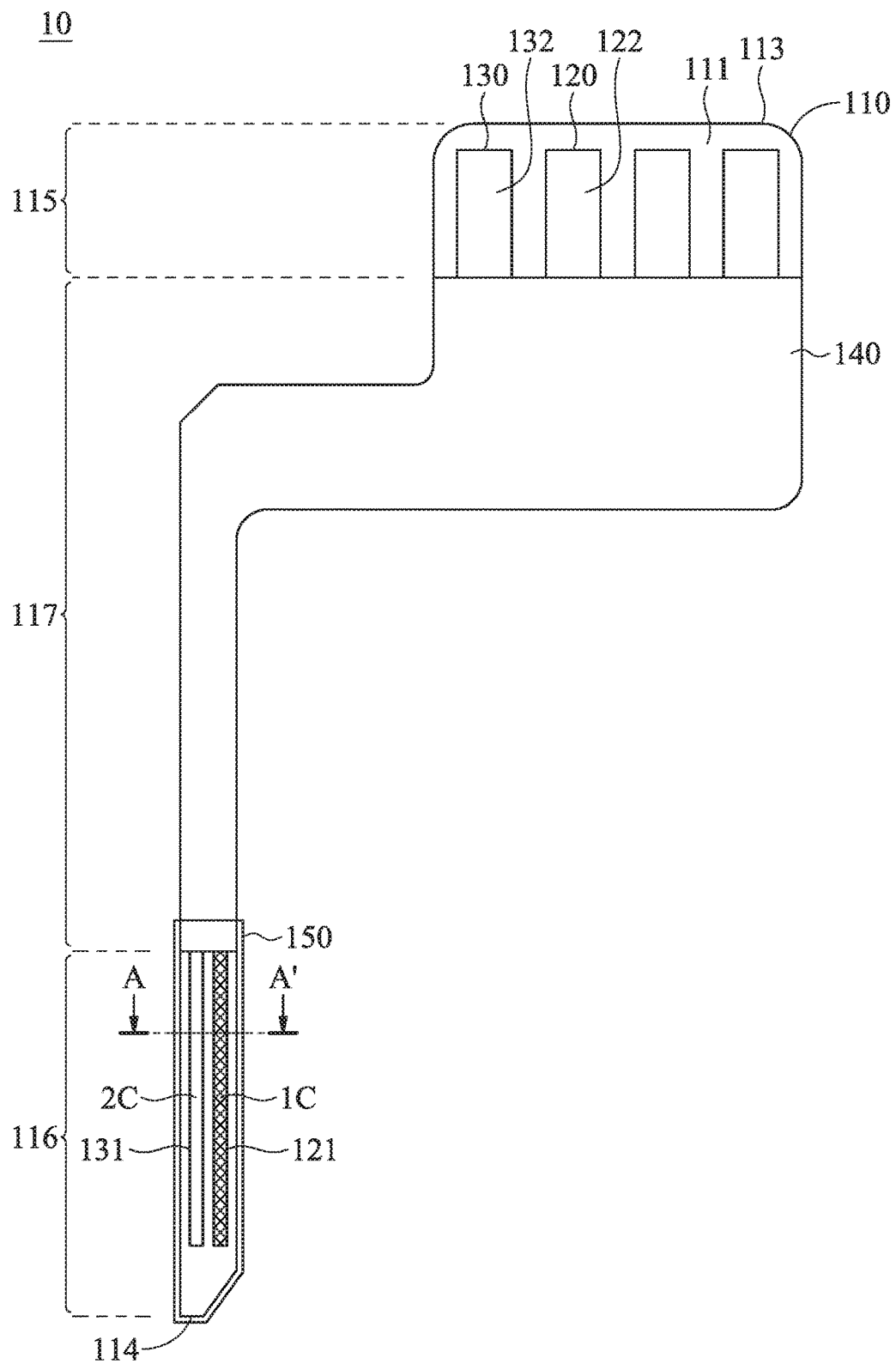
FIG. 3(A) shows a front schematic diagram of the second embodiment of the micro biosensor of the present invention.
Figure 3B:
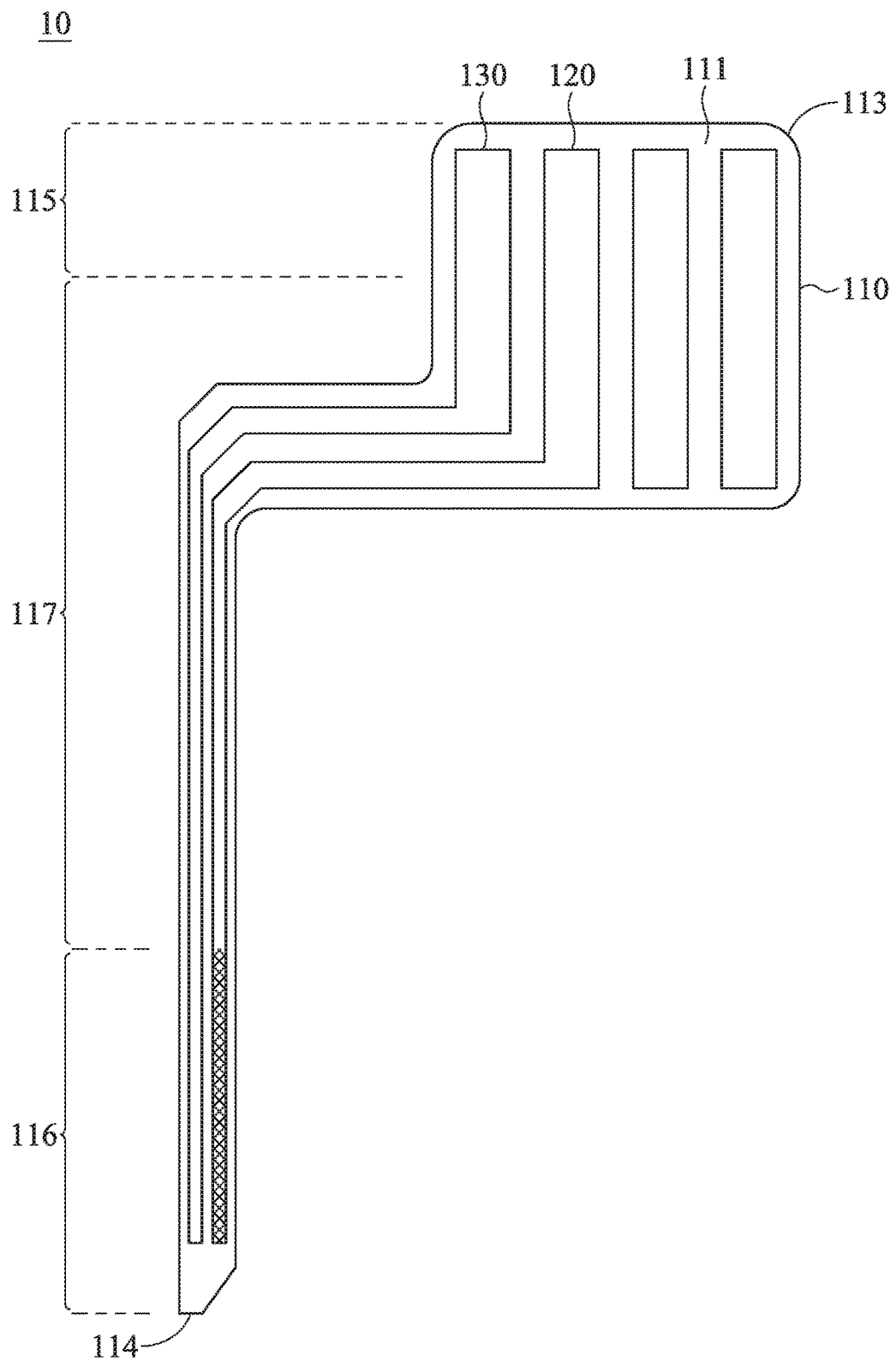
FIG. 3(B) shows a schematic diagram of the configuration of the first working electrode and the second working electrode of the second embodiment of the micro biosensor of the present invention.
Figure 4:
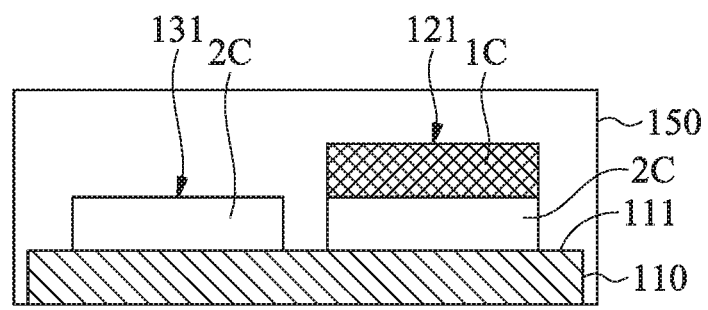
FIG. 4 shows a sectional schematic diagram of a cut view of the micro biosensor along the section line A-A' in FIG. 3(A).

Please refer to FIG. 3(A), which is a front schematic view of the second embodiment of the micro biosensor 10 of the present invention, and FIG. 3(B), which the insulating layer 14 is removed, clearly shows a configuration of the first working electrode 120 and the second working electrode 130 on the surface 111 of the substrate 110. In the second embodiment, the first working electrode 120 and the second working electrode 130 extend from the first end 113 to the second end 114 of the substrate 110. A portion of the first working electrode 120 configured in the sensing area 116 and covered by the first conductive material 1C is the first sensing section 121, and a portion of the second working electrode 130 configured in the sensing area 116 and having the second conductive material 2C is the second sensing section 131 (as shown in FIG. 3(A)). In the second embodiment, the second sensing section 131 extends along one side of the first sensing section 121 without bending so that the second sensing section 131 is only adjacent to the one side of the first sensing section 121. Therefore, the sectional schematic diagram of a cut view of the micro biosensor along the section line A-A' in FIG. 3(A) is shown in FIG. 4. The first sensing section 121 of the second embodiment of the present invention also has a first conductive material 1C covered on the second conductive material 2C, and the second sensing section 131 has a second conductive material 2C and is only adjacent to one side of the first sensing section 121.

Figure 5A:
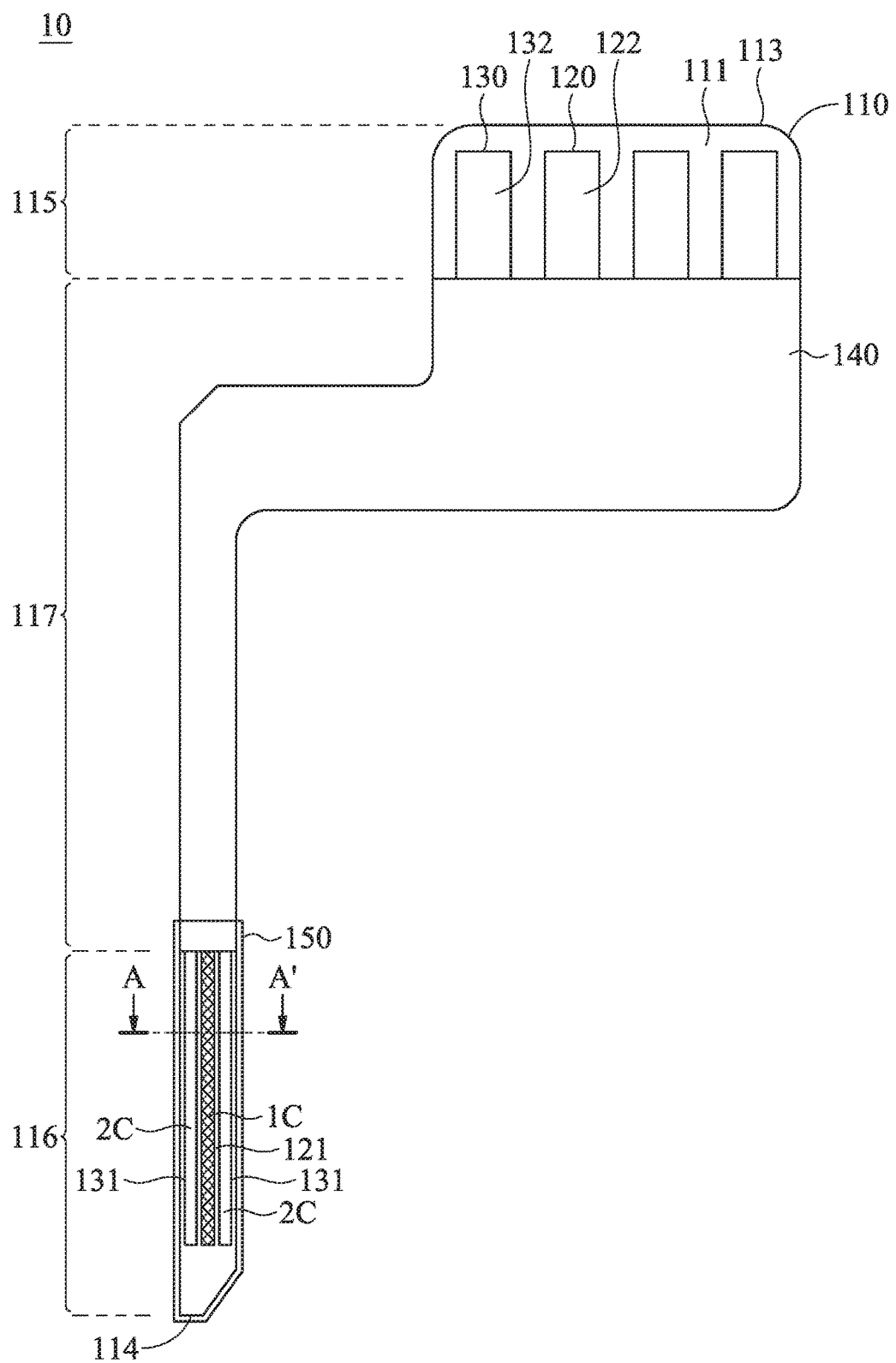
FIG. 5(A) shows a front schematic diagram of the third embodiment of the micro biosensor of the present invention.
Figure 5B:
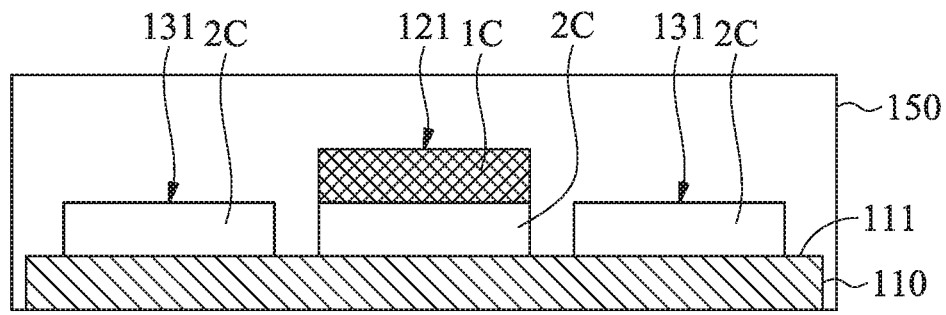
FIG. 5(B) shows a sectional schematic diagram of a cut view of the micro biosensor along the section line A-A' in FIG. 5(A).

Please refer to FIG. 5(A), which is a front schematic diagram of the third embodiment of the micro biosensor of the present invention. In the third embodiment, the micro biosensor 10 has two second working electrodes 130. The first working electrode 120 and the two second working electrodes 130 extend from the first end 113 to the second end 114 of the substrate 110, and the two second working electrodes 130 respectively extend along the two opposite sides of the first working electrode 120. The portion of the first working electrode 120 configured in the sensing area 116 and covered by the first conductive material 1C is the first sensing section 121, and the portions of the two second working electrodes 130 configured in the sensing area 116 and have the second conductive material 2C are the second sensing sections 131. In the third embodiment, the two second sensing sections 131 are respectively configured adjacent to the two opposite sides of the first sensing section 121. Therefore, the sectional schematic diagram of a cut view of the micro biosensor along the section line A-A' in FIG. 5(A) is shown in FIG. 5(B). The first sensing section 121 of the third embodiment of the present invention has a first conductive layer 1C covered on the second conductive material 2C, and the two second sensing sections 131 have second conductive materials 2C and are only adjacent to the two opposite sides of the first sensing section 121, respectively.

Figure 6A:
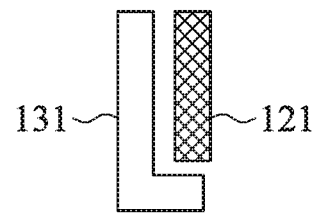
FIGS. 6(A)-6(C) show schematic diagrams of other configurations of the first sensing section and the second sensing section of the present invention.
Figure 6B:
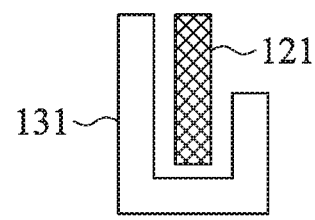
Figure 6C:
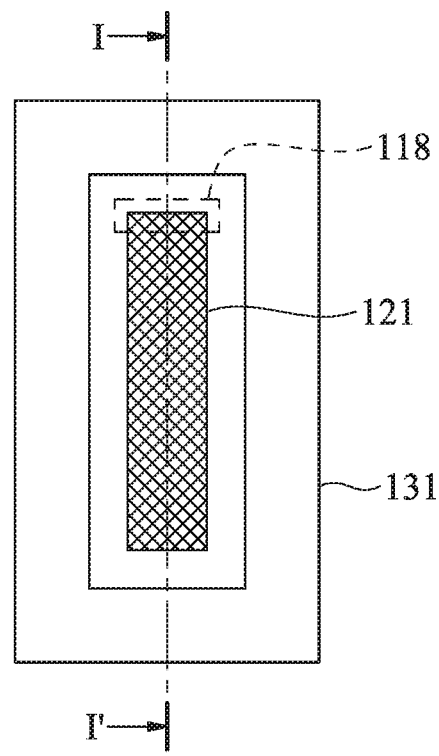
Figure 6D:
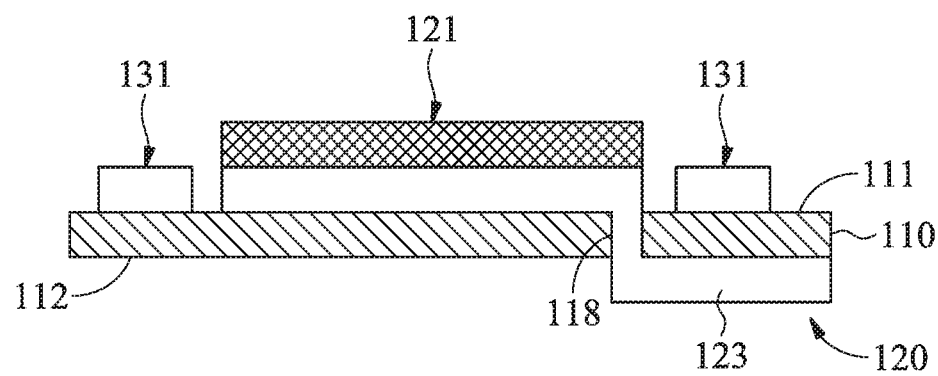
FIG. 6(D) shows a sectional schematic diagram of a cut view of the micro biosensor along the section line I-I' in FIG. 6(C).
Figure 7:
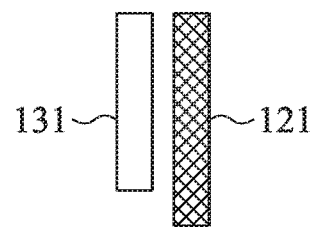
FIG. 7 shows a schematic diagram of the other configuration of the first sensing section and the second sensing section of the present invention.
Figure 8A:
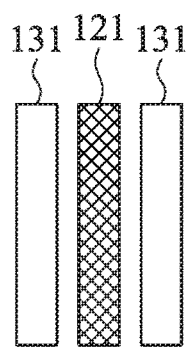
FIGS. 8(A)-8(C) show schematic diagrams of other configurations of the first sensing section and the second sensing section of the present invention.
Figure 8B:
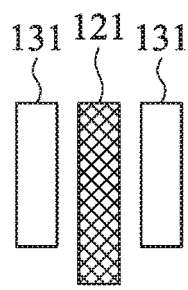
Figure 8C:
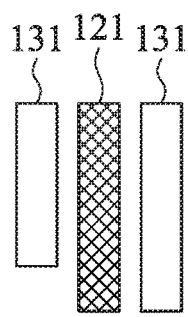

Although the configurations of the first sensing section 121 and the second sensing section 131 of the present invention are described in the first to the third embodiments, there may also be other configurations. For example, in the first embodiment, the second sensing section 131 extends along the three sides connected to each other of the first sensing section 121 and forms the U-shape sensing section. However, in an altered embodiment, the length of the second sensing section 131 extends along the three sides of the first sensing section 121 can be adjusted, as shown in FIG. 6(A), or the second sensing section 131 extends along the two adjacent sides of the first sensing section 121 so as to form an L-shape sensing section, as shown in FIG. 6(B). In another altered embodiment of the first embodiment, the first signal connecting section 123 of the first working electrode 120 can be configured and extended to the opposite surface 112 of the substrate 110 through a through hole 118 of substrate 110, and thus the second sensing section 131 can surround the four sides of the first sensing section 121, as shown in FIGS. 6(C)-6(D). Whether in the second embodiment or the third embodiment, the length of the second sensing section 131 may be altered, as shown in FIGS. 7-8(C). Therefore, the aforementioned phrase "the second sensing section 131 is adjacent to at least one side of the first sensing section 121" specifically refers that a ratio of the portion of the periphery of the first sensing section 121 adjacent to the second sensing section 131 to a total of the periphery of the first sensing section ranges from 30% to 100%.

Furthermore, as shown in FIGS. 1(A), 2(A), 3(A), 4, 5(A) and 5(B), the micro biosensor 10 of the present invention further includes a chemical reagent layer 150. The chemical reagent layer 150 at least covers the first conductive material 1C of the first sensing section 121. Specifically, in the manufacturing process of the micro biosensor 10 of the present invention, the surface 111 and/or the opposite surface 112, where already have the electrodes disposed thereon, of the substrate 110 can be immersed into a solution containing the chemical reagent. In the meanwhile, an immersion depth of the substrate 110 can be adjusted so that the chemical reagent layer 150 can be covered at least on the sensing area 116 of the micro biosensor 10 at one time. That is to say, the chemical reagent layer 150 can be both covered on the first conductive material 1C of the first sensing section 121 and the second conductive material 2C of the second sensing section 131. In other embodiment, the chemical reagent layer 150 can be further covered on the insulating area 117, as shown in FIG. 1(A). The chemical reagent layer 150 covered on the first conductive material 1C can react with the target analyte in the biofluid to produce a resultant, and the first conductive material 1C reacts with the resultant for further outputting a physiological signal corresponding to the target analyte.

The configuration of the two working electrodes disclosed in the present invention can be applied to a 2-electrode system and a 3-electrode system. In the 2-electrode system, the micro biosensor 10 of the present invention further includes at least one counter electrode 160 configured on the opposite surface 112 of the substrate 110, as shown in FIG. 9(A), which is a sectional schematic diagram of the sensing area of the micro biosensor. The counter electrode 160 can cooperate with the first working electrode 120 or the second working electrode 130. The counter electrode 160 in the 2-electrode system can also function as a reference electrode based on the material it used. The counter electrode 160 is coupled to the first working electrode 120 and/or the second working electrode 130. In other embodiments, the counter electrode 160 also can be configured on the surface 111 of the substrate 110 (figure not shown). In the 3-electrode system, apart from the counter electrode 160, the micro biosensor 10 of the present invention further includes a reference electrode 170 used for providing a reference potential, as shown in FIG. 9(B), which is a sectional schematic diagram of the sensing area 116 of the micro biosensor 10. Specifically, the counter electrode 160 and the reference electrode 170 are separate and not electrically connected, and the counter electrode 160 is coupled to the first working electrode 120 and/or the second working electrode 130. The counter electrode 160 and the reference electrode 170 also can be both configured on the surface 111 of the substrate 110 (figure not shown), or respectively configured on different surfaces of the substrate 110. In addition, as shown in FIGS. 9(A)-9(B), the chemical reagent layer 150 is also substantially covered on the counter electrode 160 and/or the reference electrode 170.

It must be noted that the term "drive" in the present invention means applying a voltage causing a potential of one electrode to be higher than a potential of the other electrode, so that the electrode with the higher potential starts the oxidation reaction. Therefore, the potential difference between the first working electrode 120 and the counter electrode 160 causing the first working electrode 120 to be driven is a first working voltage, and the potential difference between the second working electrode 130 and the counter electrode 160 causing the second electrode 130 to be driven is a second working voltage.

Figure 10:
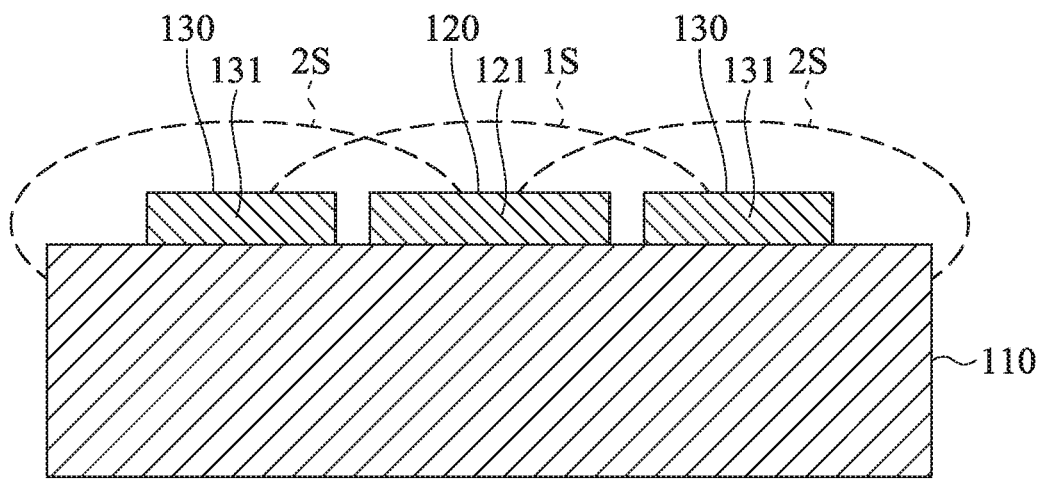
FIG. 10 shows a schematic diagram of the measurement range of the first sensing section and the interference eliminating range of the second sensing section after the micro biosensor of the present invention is driven.

Please refer to FIG. 10, the first working electrode 120 of the micro biosensor 10 of the present invention is used to measure the physiological parameter of the target analyte in the biological fluid. When the first working electrode 120 of the micro biosensor 10 is driven by the first working voltage, the first sensing section produce a measurement range 1S and has a first sensitivity to the resultant, so that the first conductive material 1C reacts with the resultant to generate a current signal. The current signal is then transmitted to the signal output section 122 of the first working electrode 120 through the signal connecting section 123, and the value of the current signal has a proportional relationship with the concentration of the resultant, so that the physiological signal corresponding to the physiological parameter is obtained. Therefore, when the first working electrode 120 is driven by the first working voltage, the action of the first conductive material 1C reacting with the resultant to output the physiological signal corresponding to the physiological parameter of the target analyte is defined as a measurement action. However, there are interferants in the biofluid, the first conductive material 1C may react with the interferants to generate an interfering current signal, and the interfering current signal and the current signal are output together to cause the physiological signal to be interfered.

Accordingly, the second working electrode 130 of the micro biosensor 10 of the present invention can be applied for consuming the interferants. When the second working electrode 130 of the micro biosensor 10 is driven by the second working voltage, the second conductive material 2C of the second sensing section 131 has a second sensitivity to the resultant, and each of the second sensing sections 131 produces an interference eliminating range 2S. Because the second sensing section 131 is disposed very close to the first sensing section 121, the interference eliminating ranges 2S, respectively, touch the periphery of the first sensing section 121 and can at least partially overlap the measurement range 1S of the first sensing section 121, so that the second conductive material 2C can consume the interferants directly and continuously by undergoing an oxidation reaction with the interferants, so as to reduce the generation of the interfering current signal, and thereby reduce the influence of the interferants on the measurement action. Therefore, when the second working electrode 130 is driven by the second working voltage, the action of causing the second conductive material 2C to consume the interferants in the living body is defined as an interference eliminating action.

Furthermore, when the second working electrode 130 is driven by the second working voltage, the second conductive material 2C may react with the resultant to generate another current signal, which will consume the resultant that should be measured by the first working electrode 120 to obtain the physiological parameter of the target analyte, so that the actual measured physiological parameter is affected. Therefore, in an embodiment, when the analyte is glucose, the resultant is hydrogen peroxide and the physiological parameter is glucose concentration, the first conductive material 1C should preferably be a material having the first sensitivity to hydrogen peroxide after being driven by the first working voltage. More preferably, the first conductive material 1C is selected from the group consisting of gold, platinum, palladium, iridium, and a combination thereof. The second conductive material 2C is different from the first conductive material 1C. Specifically, the second conductive material 2C should preferably be a material having the second sensitivity to hydrogen peroxide that is less than the first sensitivity after being driven by the second working voltage. In particular, the second conductive material 2C is a material that almost has no sensitivity to hydrogen peroxide after being driven by the second working voltage, that is, the second sensitivity is close to 0 or equal to 0. More specifically, in an embodiment in the present invention, the first conductive material 1C is platinum, the first working voltage ranges from 0.2 volts (V) to 0.8 volts (V) and preferably ranges from 0.4 volts (V) to 0.7 volts (V), and the second conductive material 2C is carbon, the second working voltage ranges from 0.2 volts (V) to 0.8 volts (V) and preferably ranges from 0.4 volts (V) to 0.7 volts (V). In another embodiment in the present invention, the first conductive material 1C is platinum, and the second conductive material 2C is gold. It must be noted that the form of the aforementioned platinum can be platinum metal, platinum black, platinum paste, other platinum-containing materials, or a combination thereof. In addition, the value of the first working voltage can be the same as that of the second working voltage, but the invention is not limited thereto.

Figure 11:
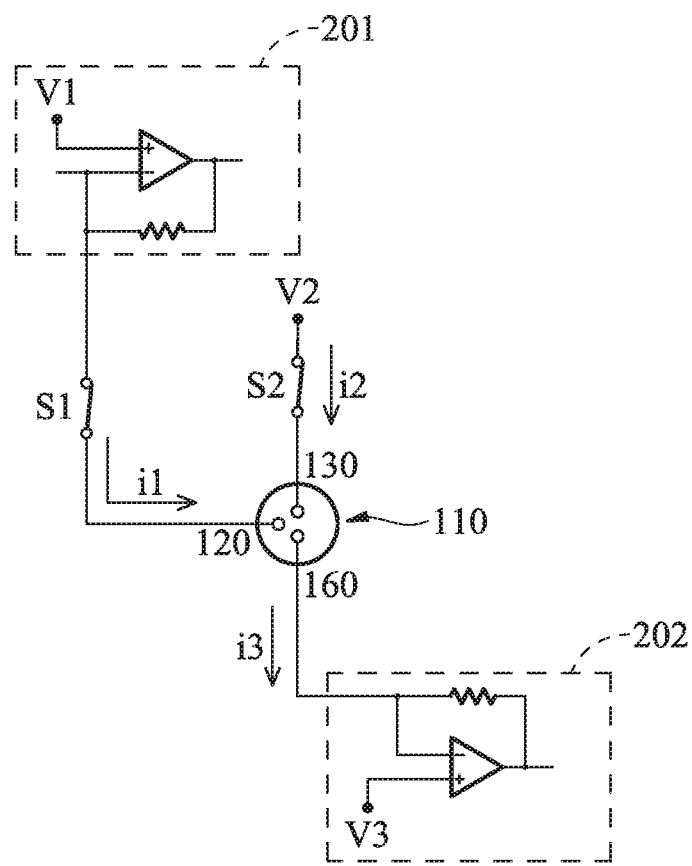
FIG. 11 shows a schematic diagram of an example of the circuit which controls voltages and measures currents of a micro biosensor of the present invention.
Figure 12:
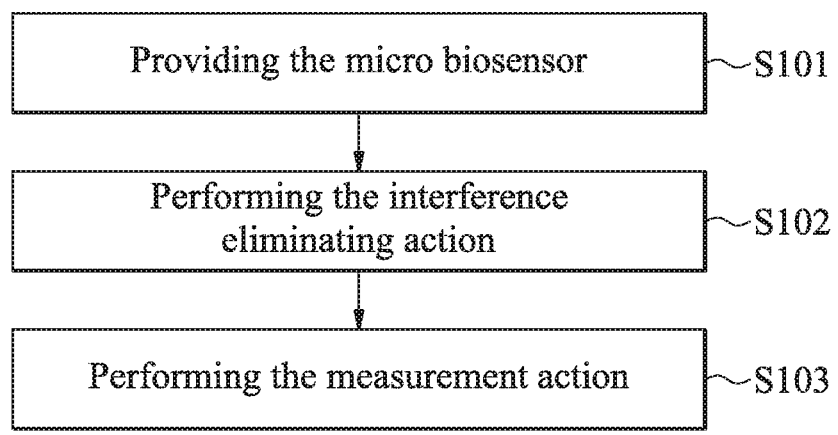
FIG. 12 shows a flowchart of a method for reducing the interference produced during the measurement of the micro biosensor of the present invention.
Figure 13A:
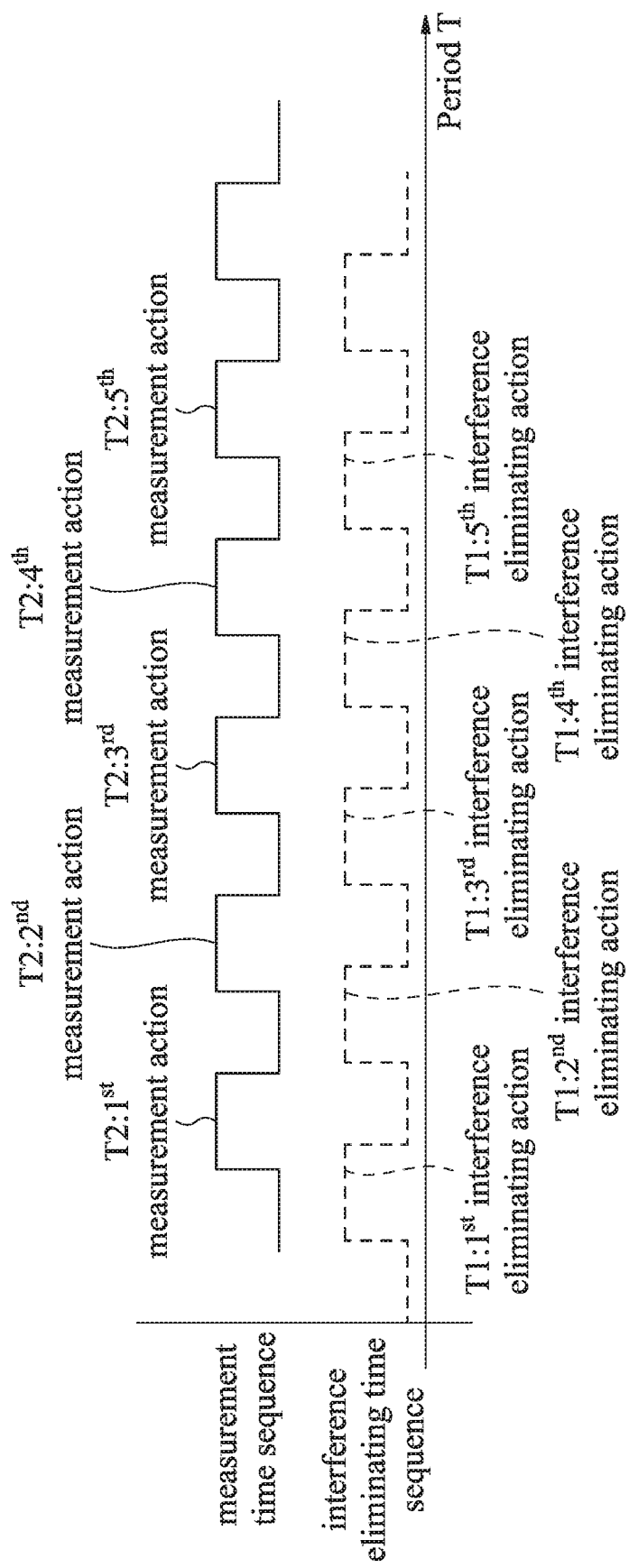
Figure 13B:
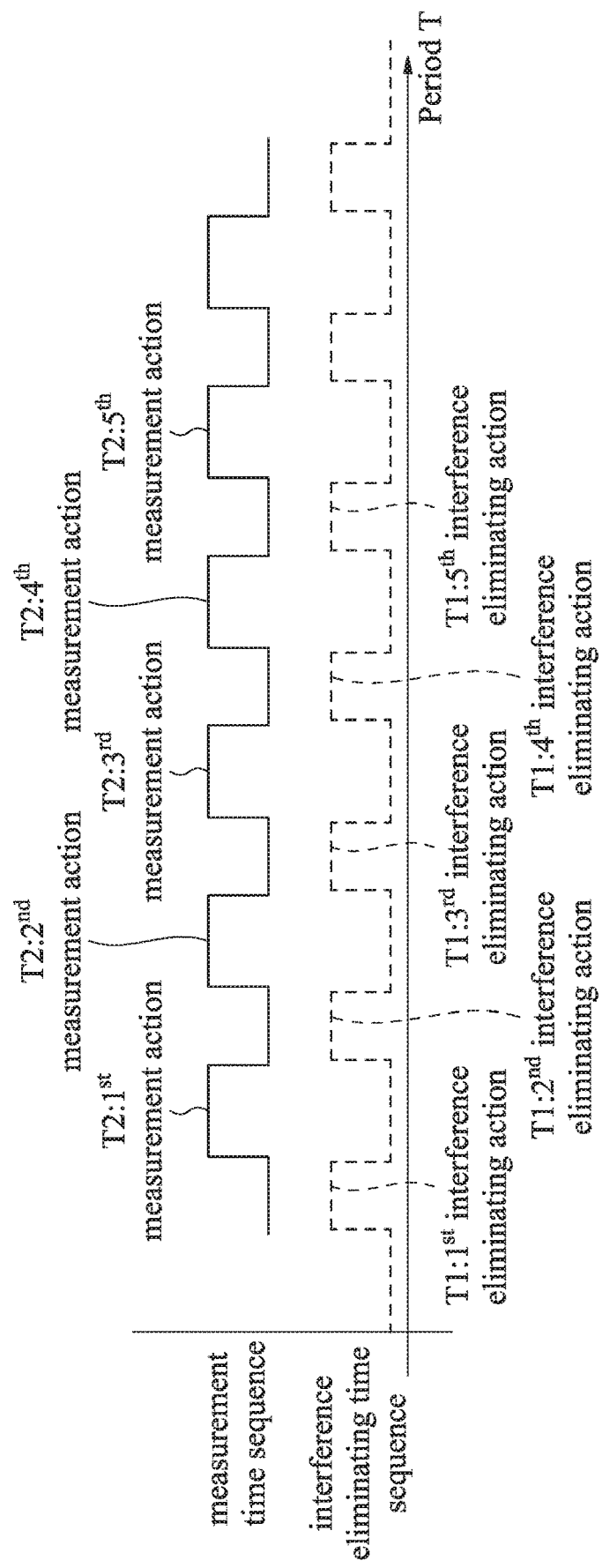
Figure 13C:
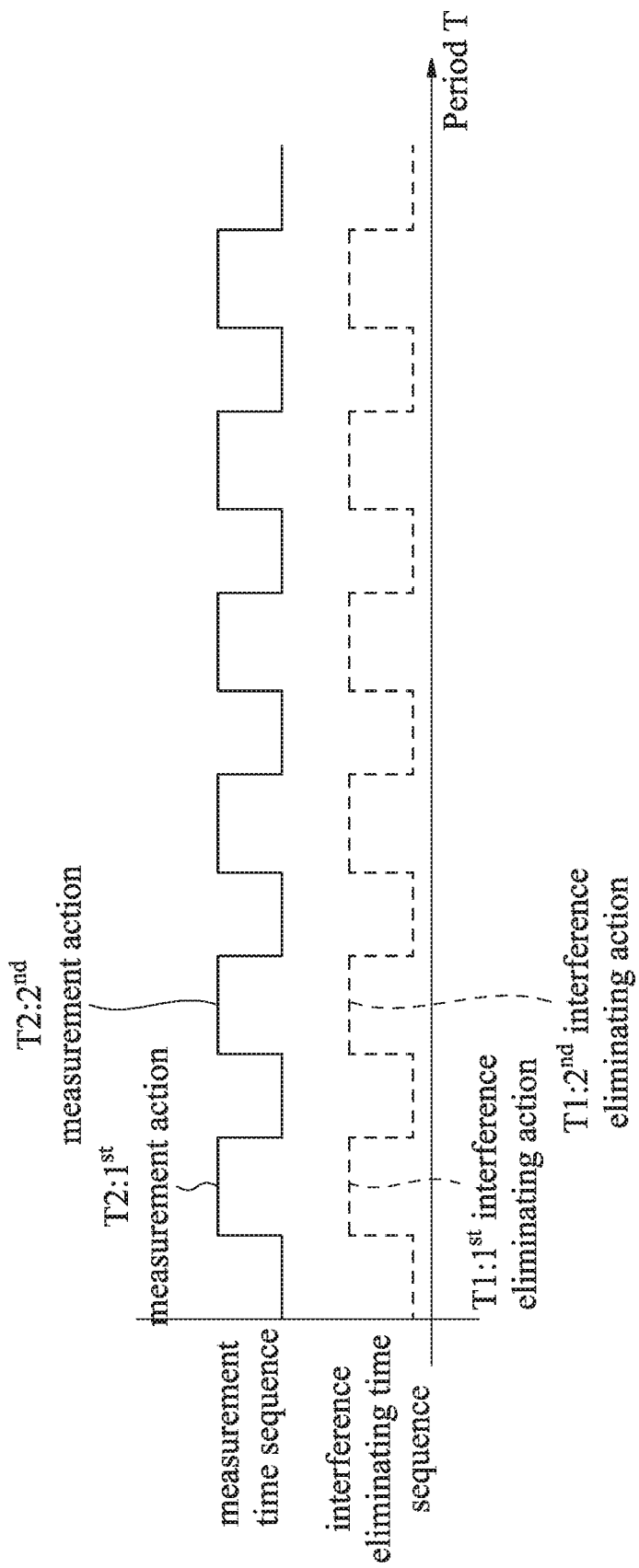

Please refer to FIGS. 11-12, which further illustrate how to operate the micro biosensor 10 of the present invention, wherein FIG. 11 is an example of the circuit which controls voltages and measures currents of the micro biosensor 10 as shown in FIG. 9(A) of the present invention, and FIG. 12 is a flowchart of a method for reducing the interference produced during the measurement of the micro biosensor 10 of the present invention. In FIG. 11, a current sensing unit 201 is connected to the first working electrode 120 of the micro biosensor 10 and another current sensing unit 202 is connected to the counter electrode 160. The current sensing units 201 and 202 measure, respectively, the current signals i1 and i3 from the first working electrode 120 and the counter electrode 160, and i2 is the current signal from the second working electrode 130, which also can be measured by another current sensing unit (figure not shown). In this example, the first working voltage is a difference between a potential V1 of the first working electrode 120 and a potential V3 of the counter electrode 160, and the second working voltage is a difference between a potential V2 of the second working electrode 130 and the potential V3 of the counter electrode 160. Switches S1 and S2 allow, respectively, the first working electrode 120 and the second working electrode 130 to be set floating. The method for reducing the measurement interference of the present invention is shown in FIG. 12, and includes providing the micro biosensor (Step 101), performing the interference eliminating action (Step 102), and performing the measurement action (Step 103). There is a time relationship between the interference eliminating action and the measurement action, and the possible time sequences respectively are:

The first time relationship: the micro biosensor of the present invention performs a measurement during a period T, such as 2 weeks, and the period T includes a plurality of first sub-time (T1) zones and/or a plurality of second sub-time (T2) zones. The interference eliminating action is performed in each T1 zone, and the measurement action is performed in each T2 zone. The interference eliminating action and the measurement action are performed alternately. That is to say, the first time relationship is that sequentially performing the first interference eliminating action in the first T1 zone to consume the interferant, performing the first measurement action in the first T2 zone to output a first physiological signal corresponding to the then-current physiological parameter, performing the second interference eliminating action in the second T1 zone to consume the interferant, performing the second measurement action in the second T2 zone to output a second physiological signal corresponding to the then-current physiological parameter, and so on, to obtain value data of the physiological parameter in all respective T2 zones during the period T. As shown in FIGS. 13(A)-13(C), the horizontal and vertical axles of the figures respectively represent time and current, in which the line of the measurement action shows the application and remove of the first working voltage, and the other line of the interference eliminating action shows the application and remove of the second working voltage. In the first time relationship, the T1 zone and the T2 zone can be at least partially overlap (as shown in FIG. 13(A)), the T1 zone and the T2 zone can be separated from each other (as shown in FIG. 13(B)), or the T1 zone and the T2 zone are completely overlapped, that is, the measurement action and the interference eliminating action can be performed at the same time (as shown in FIG. 13(C)). In the period T, the second working voltage can be removed between any two T1 zones to stop the interference eliminating action toseparate the two T1 zones, and the first working voltage can be removed between any T2 zones to stop the measurement action to separate the two T2 zones. In the first time relationship, the duration of the T1 zone is conditioned to allow the current signal to correspond to the concentration of the resultant and have the proportional relationship with the physiological parameter. The duration of the T1 zone can be the same as that of the T2 zone or longer than that of the T2 zone to achieve the effective interference consumption.

Furthermore, as shown in FIGS. 13(A)-13(B), the first interference eliminating action will be preferably acted earlier than or simultaneous with the first measurement action. Specifically, when there are multiple measurement actions, the interference eliminating action is executed at least once and preferably, the startup of the interference eliminating action is no later than the beginning of the first measurement action of the multiple measurement actions.

Figure 14:
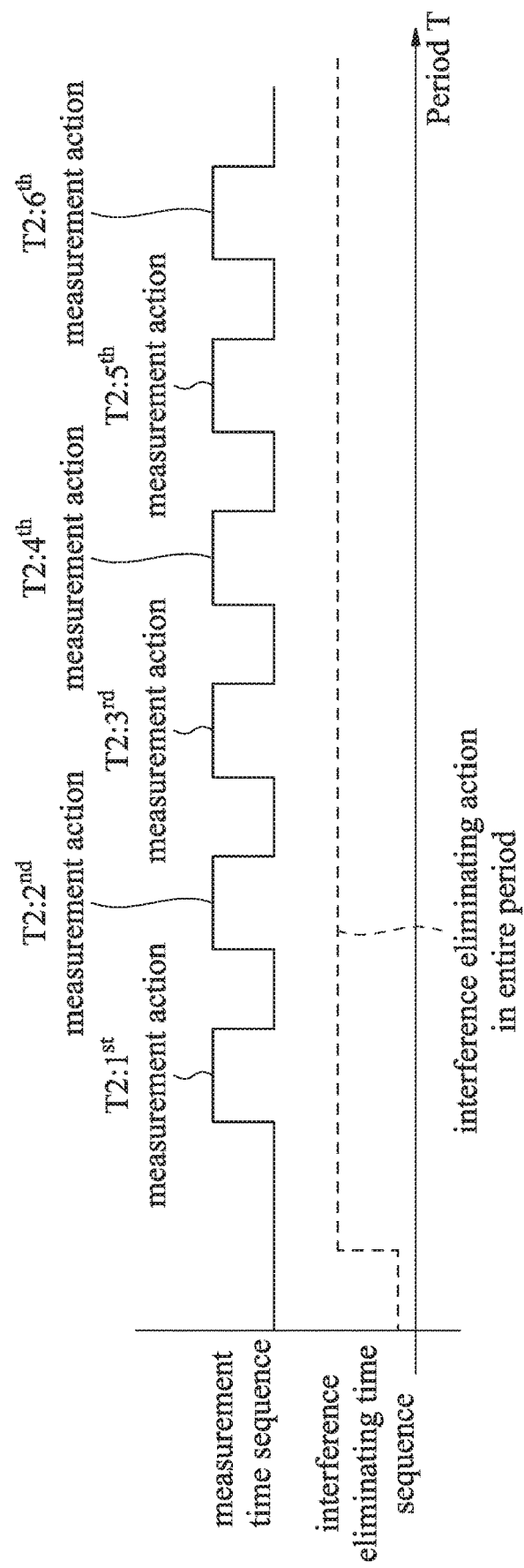
FIG. 14 shows a schematic diagram of the time relationship between the interference eliminating action and the measurement action during measurement using the micro biosensor of the present invention.

The second time relationship: the micro biosensor of the present invention performs a measurement during a period T, such as 2 weeks, and the period T includes a plurality of sub-time zones. The interference eliminating action is performed in the entire period T, and the measurement action is performed in each the sub-time zone. The measurement action is performed at intervals. That is to say, please refer to FIG. 14, the second time relationship is that continuous performing the first interference eliminating action in the entire period T to consume the interferant until the end of the period T, and in the interference eliminating action is performed, performing the first measurement action in the first sub-time zone to output a first physiological signal corresponding to the then-current physiological parameter, performing the second measurement action in the second sub-time zone to output a second physiological signal corresponding to the then-current physiological parameter, and so on, to obtain value data of the physiological parameters in all different sub-time zones during the period T. There is a time interval between two adjacent sub-time zones. In the period T, the first working voltage can be removed between any two sub-time zones to stop the measurement action to separate the two sub-time zones. In the second time relationship, the duration of each sub-time zone can be the same or different, and the duration of each sub-time zone is conditioned to allow the current signal to correspond to the concentration of the resultant and have the proportional relationship with the physiological parameter.

The third time relationship: although the figure is not shown, the difference between the third time relationship and the second time relationship is that the third time relationship continuous performing the measurement action in the entire period T, and performing the interference eliminating action in every sub-time zones. That is to say, the interference eliminating action is performed alternatively.

Figure 15:
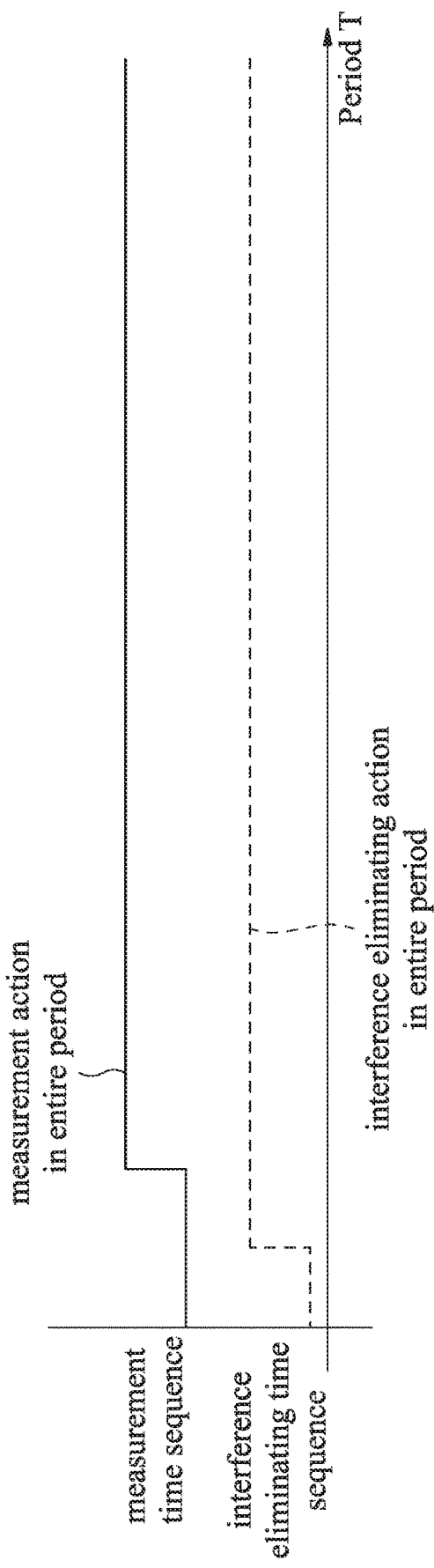
FIG. 15 shows a schematic diagram of the time relationship between the interference eliminating action and the measurement action during measurement using the micro biosensor of the present invention.

The fourth time relationship: please refer to FIG. 15, the micro biosensor of the present invention performs a measurement during a period T, such as 2 weeks. The interference eliminating action is continuously performed in the entire period T, and simultaneously, the measurement action is also continuously performed until the end of the period T to continuously consume the interferant and measure the physiological parameter.

Interference Eliminating Test In Vitro

Test Example

In this test example, the micro biosensor of the first embodiment having the two working electrodes is used, wherein the first sensing section is a carbon electrode coated with platinum black, the second sensing section is a carbon electrode, the first working voltage is 0.5V, the second working voltage is 0.5V and the interferant is acetaminophen.

Comparative Test Example

Figure 16:
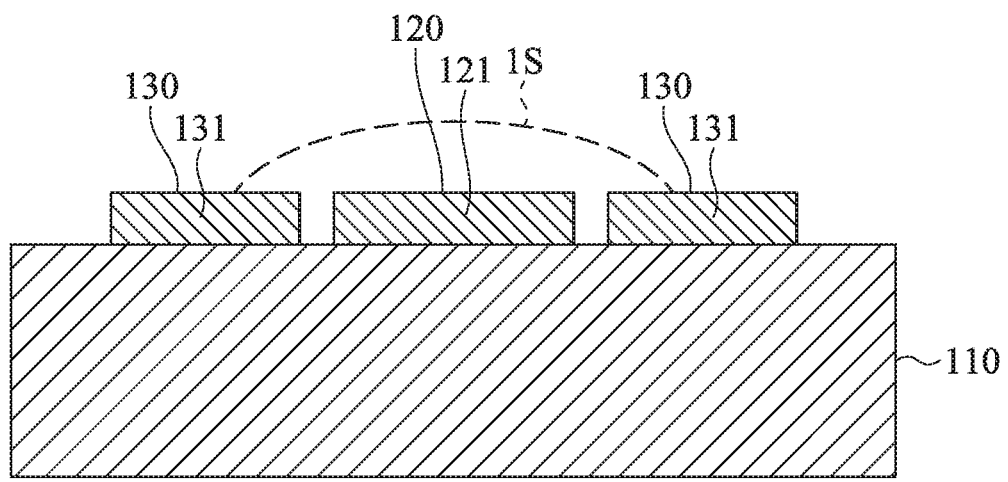
FIG. 16 shows a schematic diagram of the measurement range of the first sensing section after only the first sensing section of the micro biosensor of the present invention is driven.

In this comparative test example, the micro biosensor used in the comparative test example is the same as the test example, but no second working voltage is provided. Because no second working voltage is provided, the second sensing section 131 does not be driven, and thus only the measurement range 1S of the first sensing section is existed, as shown in FIG. 16.

The method of the interference eliminating test in vitro using the micro biosensor of the present invention is as follows. The micro biosensors of the test example and the comparative test example are sequentially immersed in phosphate buffered saline (PBS) solution, 100 mg/dL glucose solution, 40 mg/dL glucose solution, 100 mg/dL glucose solution, 300 mg/dL glucose solution, 500 mg/dL glucose solution, 100 mg/dL glucose solution, 100 mg/dL glucose solution with 2.5 mg/dL acetaminophen, 100 mg/dL glucose solution, and 100 mg/dL glucose solution with 5 mg/dL acetaminophen at different time periods (P1 to P9). The results are shown in FIG. 17, wherein the current signal measured from the first sensing section 121 is shown as a curve C1 and the current signal measured from the second sensing section 131 is shown as a curve C2 in the test example, and the current signal measured from the first sensing section 121 of the comparative test example is shown as curve C3.

Figure 17:
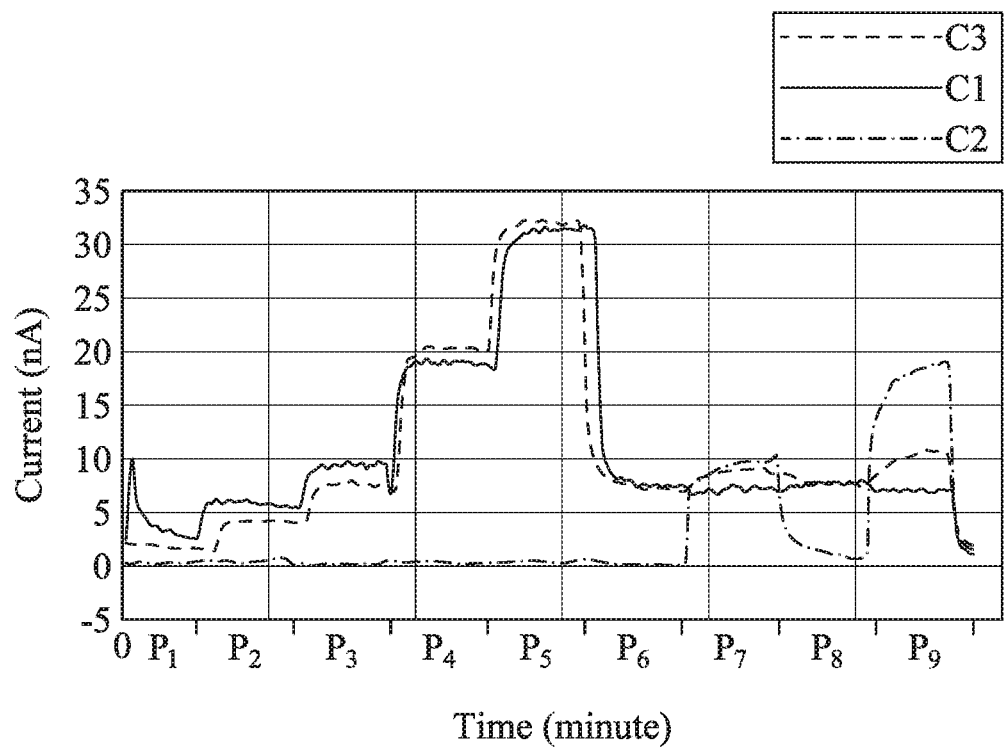
FIG. 17 shows a measurement curve diagram illustrating of the application of a test example of the present invention and a comparative test example to the interference elimination test in vitro, wherein when the interference eliminating function of the second working electrode is activated, a current signal measured from the first sensing section is presented as a curve C1, and a current signal measured from the second sensing section is presented as a curve C2; and when the interference eliminating function of the second working electrode is not activated, a current signal measured by the first sensing section is presented as a curve C3.

It can be seen from time periods P1 to P5 in FIG. 17 that regardless of the test example or the comparative test example, the first sensing section produces current signals with different intensities according to the different glucose concentrations at different time periods. That is to say, there is the proportional relationship between the current signals of the first sensing section and the physiological parameter. However, there is no current signal produced from the second sensing section, which represents that the activity or the sensitivity of the second sensing section to hydrogen peroxide, a by-product derived from glucose catalyzed by enzymes, is very low, close to 0 or equal to 0. In addition, it can be seen from the curve C3 that when the micro biosensors of the comparative test example are immersed in the 100 mg/dL glucose solution with 2.5 mg/dL acetaminophen at the time period P7, comparing to the current signal measured at the time period P3, the current signal measured by the first sensing section 121 at the time period P7 is obviously affected by the interferant and floats high, and the level of the measurement interference is more obvious when the micro biosensor is immersed in the 100 mg/dL glucose solution with 5 mg/dL acetaminophen at the time period P9. On the contrary, it can be seen from the curve C1 and the curve C2 that when the micro biosensor of the test example is immersed in the 100 mg/dL glucose solution with 2.5 mg/dL acetaminophen at the time period P7, the current signal at the time period P7 is consistent with that at the time period P3. Specifically, when the second working electrode 130 is driven by the second working voltage to perform the interference eliminating action, the level to which the first sensing section 121 is affected by acetaminophen can be reduced, even if the concentration of acetaminophen is increased. On the other hand, because the second sensing section 131 of the second working electrode 130 is used to consume acetaminophen, there is no current signal produced in the PBS solution and the glucose solution, but a current signal will be produced when there is acetaminophen. Therefore, when there is acetaminophen in the measurement environment (i.e. the measurement range), the second sensing section 131 can consume acetaminophen to reduce the measurement of the first sensing section interfered by acetaminophen, and thereby the micro biosensor can measure more accurate physiological parameters.

Interference Eliminating Test In Vivo

In this interference eliminating test in vivo, the micro biosensor of the first embodiment having the two working electrodes of the present invention is used, wherein the first sensing section is a carbon electrode coated with platinum black, the second sensing section is a carbon electrode, the first working voltage is 0.5V, and the second working voltage is 0.5V. The micro biosensor is implanted under the human skin to continuously monitor the glucose concentration in the interstitial fluid, and 1 g panadol, which main component is acetaminophen, is administered at the $86^{th}$ hour. The data with and without the interferant eliminating mechanism are measured, and compared with the data measured by the traditional blood glucose meter. The results are shown in FIGS. 18(A)-18(B), wherein FIG. 18(A) is the measurement curve without the interferant eliminating mechanism, and FIG. 18(B) is the measurement curve with the interferant eliminating mechanism.

Figure 18A:
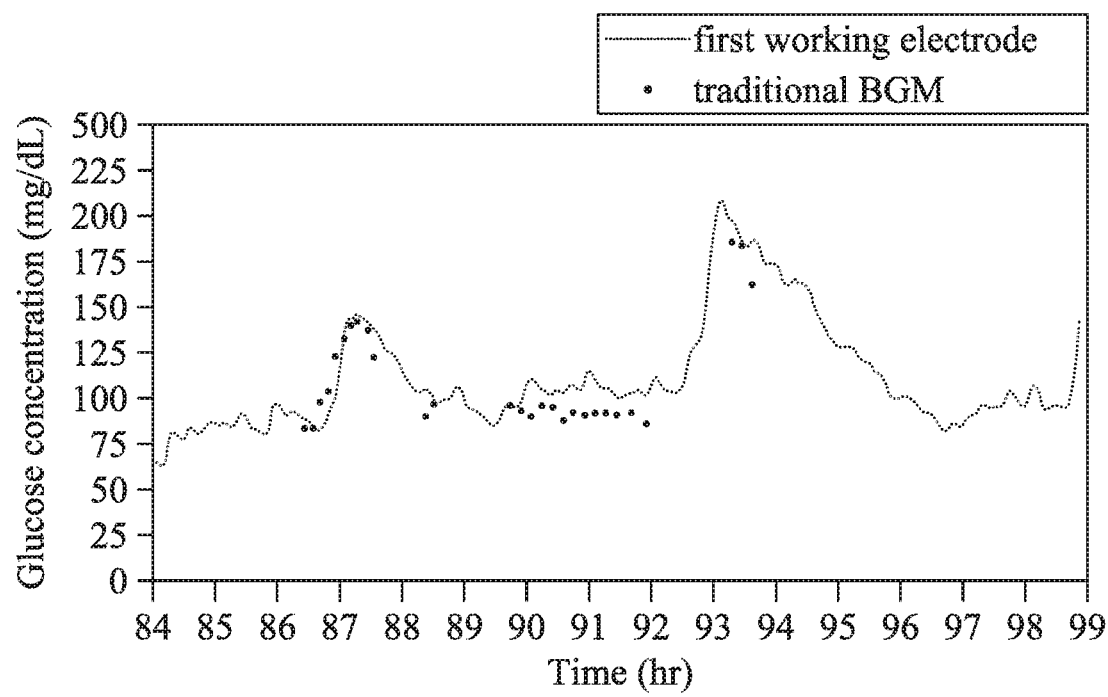
Figure 18B:
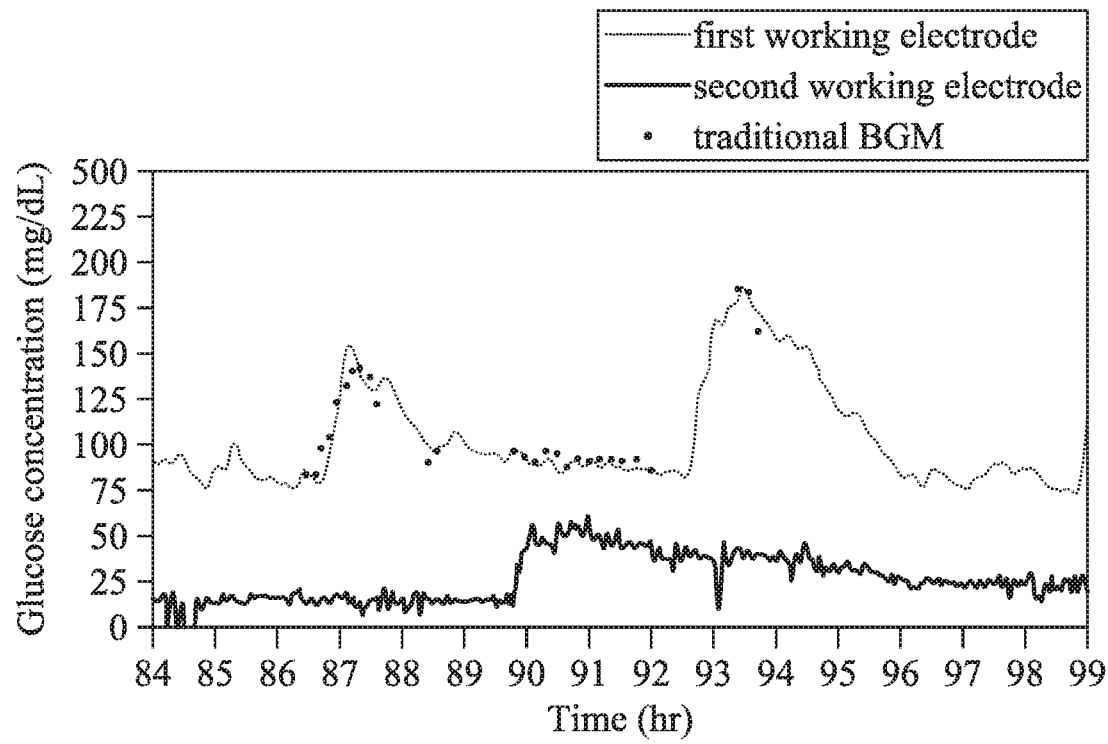

In FIGS. 18(A)-18(B), the black points are values measured by the traditional blood glucose meter, the dotted line is the measurement curve of the first working electrode of the micro biosensor of the present invention, and the solid line is the measurement curve of the second working electrode of the micro biosensor of the present invention. It can be seen from FIG. 18(A) that when the interference eliminating action is not activated, the values measured by the first working electrode of the micro biosensor of the present invention is increased around the $90^{th}$-$96^{th}$ hour (i.e. after 1 g panadol is administered 4-6 hours). On the contrary, it can be seen from FIG. 18(B) that when the interference eliminating action is activated, the second sensing section of the micro biosensor of the present invention measures the corresponding current signals, and the values measured by the first working electrode is not increased, and can be matched with the measuring values using the traditional blood glucose meter.

In addition, when the interference eliminating function of the micro biosensor is activated, an average error value during the period without drug interference is 0.1 mg/dL, an average error value during the period with drug interference is −2.1 mg/dL, a total error value is −1.1 mg/dL, and a mean absolute relative difference (MARD) during the period with drug interference is 4.6. When the interference eliminating function of the micro biosensor is not activated, the average error value during the period without drug interference is −0.2 mg/dL, the average error value during the period with drug interference is 12.6 mg/dL, the total error value is 6.7 mg/dL, and the mean absolute relative difference (MARD) during the period with drug interference is 10.6. It can be seen that the interference eliminating action of the second sensing section 131 of the second working electrode 130 can indeed reduce the interference of the interferants on the physiological signal measured by the first sensing section 121 to less than or equal to a specific tolerance scope, such as 20%, and more specifically 10%. In summary, the present invention using the micro biosensor which the second sensing section is configured adjacent to at least one side of the first sensing section, which cause the second sensing section to directly and continuously consume the interferant around the first sensing section, so as to reduce the measurement interference of the interferant on the first sensing section to obtain more accurate data.

Although the present invention has been described with reference to certain exemplary embodiments thereof, it can be understood by those skilled in the art that a variety of modifications and variations may be made to the present invention without departing from the spirit or scope of the present invention defined in the appended claims, and their equivalents.

What is claimed is:

1. A micro biosensor for implantation under a skin to perform a measurement of a physiological parameter of a target analyte in a biofluid and reduce an interference of at least one interferant in the biofluid on the measurement, the micro biosensor comprising:
   a substrate having a surface;
   a first working electrode including a first sensing section configured on the surface, wherein the first sensing section includes a first conductive material;
   at least one second working electrode configured on the surface and including a second sensing section configured adjacent to the first sensing section of the first working electrode and surrounds three sides of the first sensing section to form a U-shape structure, wherein the second sensing section includes a second conductive material different from the first conductive material; and
   a chemical reagent covered on at least a portion of the first conductive material for reacting with the target analyte in the biofluid to produce a resultant, wherein:
   the first working electrode is driven by a first working voltage to cause the first conductive material, having a first sensitivity to the resultant and producing a measurement range, to react with the resultant for outputting a physiological signal corresponding to the physiological parameter of the target analyte; and
   the second working electrode is driven by a second working voltage to allow the second conductive material, having a second sensitivity to the resultant smaller than the first sensitivity and producing an interference eliminating range, wherein the U-shape structure enables the interference eliminating range to at least partially overlap with the measurement range to directly consume the interferant for reducing a generation of an interfering current signal at the first working electrode.

2. The micro biosensor as claimed in claim 1, wherein, when the first working electrode is driven by the first working voltage, the first conductive material has the first sensitivity to the resultant, and when the second working electrode is driven by the second working voltage, the second conductive material has the second sensitivity to the resultant.

3. The micro biosensor as claimed in claim 1, wherein a value of the first working voltage is the same as that of the second working voltage.

4. The micro biosensor as claimed in claim 1, wherein the second sensing section is configured adjacent to the at least one side of the first sensing section with a gap, and the gap is no larger than 0.2 mm.

5. The micro biosensor as claimed in claim 1, wherein a number of the second working electrode is two, and the two second sensing sections of the two second working electrodes are respectively configured adjacent to the two opposite sides of the first sensing section of the first working electrode.

6. The micro biosensor as claimed in claim 1, wherein the first sensing section and the second sensing section maintain a positional relationship therebetween only via the surface.

7. The micro biosensor as claimed in claim 1, wherein the second sensing section is configured directly adjacent to at least one side of the first sensing section without any other electrode between the first working electrode and the at least one second working electrode.

8. The micro biosensor as claimed in claim 1, wherein the second working electrode directly consumes the interferant to reduce the interfering current signal at the first working electrode without outputting an interfering current signal from the second working electrode.

9. A method for reducing a measurement interference of a target analyte, comprising:
   providing a micro biosensor used to measure a physiological parameter of a target analyte in a biofluid, wherein the micro biosensor comprises:
      a substrate having a surface;
      a first working electrode including a first sensing section configured on the surface, wherein the first sensing section includes a first conductive material;
      at least one second working electrode configured on the surface and including a second sensing section, wherein the second sensing section includes a second conductive material different from the first conductive material; and
      a chemical reagent covered on at least a portion of the first conductive material for reacting with the target analyte in the biofluid to produce a resultant;
   performing an interference eliminating action, wherein the first conductive material having a first sensitivity to the resultant, wherein the interference eliminating action is to drive the second working electrode by a second working voltage to cause the second conductive material, having a second sensitivity to the resultant smaller than the first sensitivity, to directly consume an interferant in the biofluid for reducing a generation of an interfering current signal at the first working electrode; and
   performing a measurement action, wherein the measurement action is to drive the first working electrode by a first working voltage to cause the first conductive material to react with the resultant to output a physiological signal corresponding to the physiological parameter of the target analyte,
      wherein a time period for performing the interference eliminating action is at least partially overlapped with a time period for performing the measurement action.

10. The method as claimed in claim 9, wherein the interference eliminating action and the measurement action are performed simultaneously.

11. The method as claimed in claim 9, wherein, when there are multiple measurement actions, the interference eliminating action is executed at least once and a startup of the interference eliminating action is no later than a beginning of a first measurement action of the multiple measurement actions.

12. The method as claimed in claim 9, wherein, when the interference eliminating action is only performed once, a startup of the interference eliminating action is at least earlier than a measurement period of the measurement action that is a single measurement action.

13. The method as claimed in claim 9, wherein the second sensing section is configured adjacent to the at least one side of the first sensing section with a gap, and the gap is no larger than 0.2 mm.

14. The method as claimed in claim 9, wherein the micro biosensor further comprises at least one counter electrode coupled to at least one of the first working electrode and the second working electrode, and the step of performing the measurement action is completed by the first working electrode and the counter electrode.

15. The method as claimed in claim 9, wherein the second sensing section of the second working electrode surrounds at least three sides of the first sensing section of the first working electrode to form a U-shape structure.

* * * * *